United States Patent
Olson et al.

(10) Patent No.: US 6,551,273 B1
(45) Date of Patent: Apr. 22, 2003

(54) CATHETER HAVING A SHAFT KEEPER

(75) Inventors: Richard J. Olson, Plymouth, MN (US); Jason Lenz, Maplewood, MN (US); Loren J. Simer, Jr., Minnetonka, MN (US); Paul J. Miller, St. Paul, MN (US); Katherine M. Prindle, Robbinsdale, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 29 days.

(21) Appl. No.: 09/644,753

(22) Filed: Aug. 23, 2000

(51) Int. Cl.[7] .............................................. A61M 29/00
(52) U.S. Cl. ........................ 604/103.03; 604/27; 24/335
(58) Field of Search .......................... 604/27, 103.03, 604/103.09, 96.01, 524, 533, 530; 24/326, 335, 339, 343, 112, 130, 129 C

(56) References Cited

U.S. PATENT DOCUMENTS

| | | | |
|---|---|---|---|
| 3,251,069 A | 5/1966 | Clark | |
| 4,029,103 A | 6/1977 | McConnell | |
| 4,419,094 A | 12/1983 | Patel | |
| 4,612,053 A | 9/1986 | Brown et al. | 706/35 |
| 5,191,888 A | 3/1993 | Palmer et al. | |
| 5,364,355 A | 11/1994 | Alden et al. | 604/96 |
| 5,366,444 A | 11/1994 | Martin | 604/159 |
| 5,372,592 A | 12/1994 | Gambale | 604/280 |
| 5,438,993 A | 8/1995 | Lynch et al. | 128/657 |
| 5,545,254 A | 8/1996 | Chow et al. | 106/35 |
| 5,605,713 A | 2/1997 | Boltong | 427/2.1 |
| 5,652,016 A | 7/1997 | Imura et al. | 427/212 |
| 5,695,729 A | 12/1997 | Chow et al. | 423/305 |
| 5,730,150 A | 3/1998 | Peppel et al. | 128/772 |
| 5,782,971 A | 7/1998 | Constantz et al. | 106/690 |
| 5,820,632 A | 10/1998 | Constantz et al. | 623/16 |
| 5,827,202 A | 10/1998 | Miraki et al. | 600/585 |
| 5,830,183 A | 11/1998 | Krieger | 604/96 |
| 5,944,701 A | 8/1999 | Dubrul | 604/264 |
| 5,954,707 A | 9/1999 | Kanesaka et al. | 604/523 |
| 5,978,699 A | 11/1999 | Fehse et al. | 600/434 |
| 6,005,162 A | 12/1999 | Constantz | 623/16 |
| 6,027,742 A | 2/2000 | Lee et al. | 424/422 |
| 6,074,368 A | 6/2000 | Wright | |
| 6,117,456 A | 9/2000 | Lee et al. | 424/602 |
| 6,132,463 A | 10/2000 | Lee et al. | 623/16 |
| 6,139,578 A | 10/2000 | Lee et al. | 623/16.11 |

FOREIGN PATENT DOCUMENTS

| | | |
|---|---|---|
| DE | 198 23 064 A1 | 11/1999 |
| FR | 2 633 178 A1 | 12/1989 |
| JP | 111332992 | 7/1999 |
| WO | WO 99/45997 A1 | 9/1999 |
| WO | WO 99/47202 A1 | 9/1999 |
| WO | WO 99/55409 A1 | 11/1999 |

*Primary Examiner*—Chen-Wen Jiang
(74) *Attorney, Agent, or Firm*—Crompton, Seager & Tufte, LLC

(57) ABSTRACT

Devices and methods for managing a portion of an intravascular catheter which is extending from the body of a patient under operating room conditions (e.g., while a physician is wearing surgical gloves). A catheter in accordance with one embodiment of the present invention includes a catheter shaft having a proximal end and a distal end, and a keeper fixed to the catheter proximate a proximal end thereof The keeper includes one or more inside surfaces defining a channel which is adapted to entrap a straight portion of the catheter shaft. The keeper also includes a passageway which is adapted to allow a curved portion of the catheter to pass into the channel of the keeper.

25 Claims, 18 Drawing Sheets

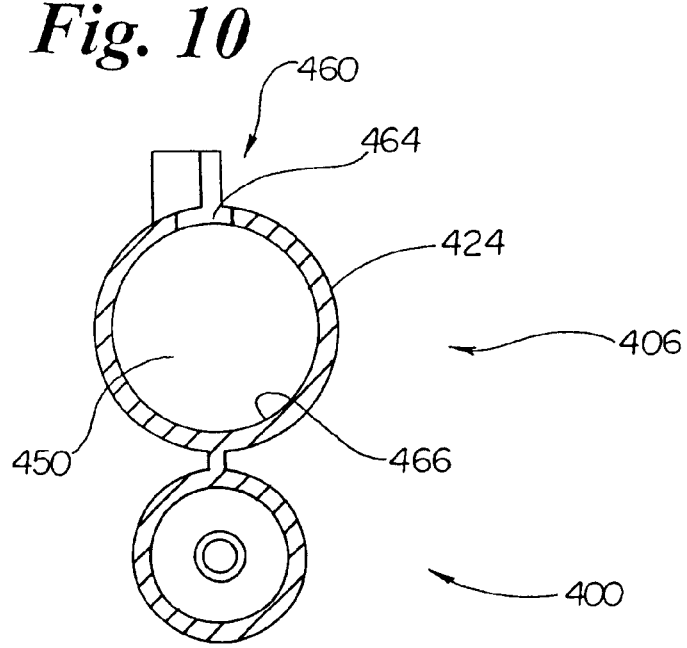
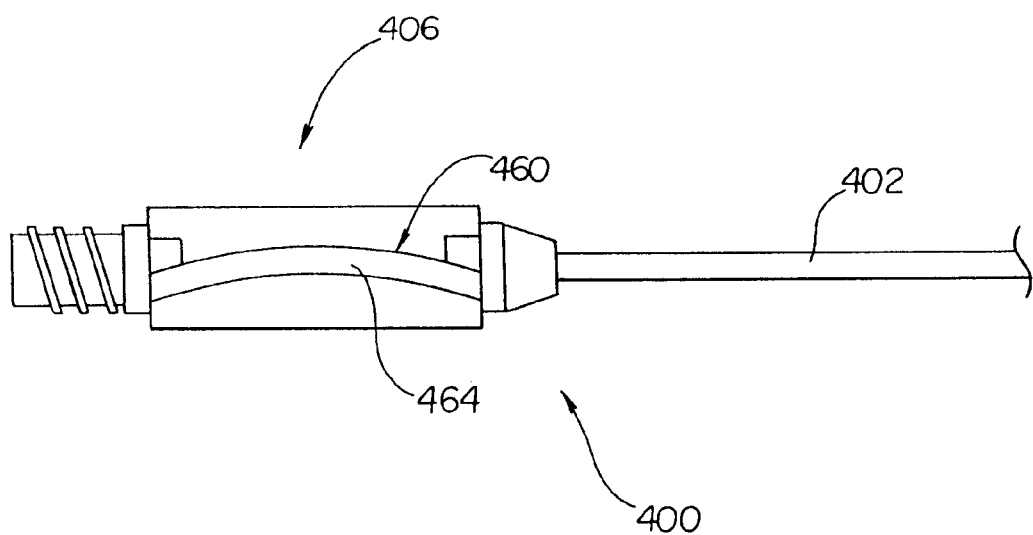

CATHETER HAVING A SHAFT KEEPER

FIELD OF THE INVENTION

The present invention relates generally to catheters for performing medical procedures. More particularly, the present invention relates to methods and devices for managing a portion of the catheter which extends from the body of a patient under operating room conditions (e.g., while the physician is wearing surgical gloves).

BACKGROUND OF THE INVENTION

Intravascular catheters are currently utilized in a wide variety of minimally invasive medical procedures. Generally, an intravascular catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed, including the coronary, cerebral, and peripheral vasculature.

Intravascular catheters are often used in conjunction with a guidewire. When this is the case, the guidewire may be advanced through the patient's vasculature until its distal tip has reached a desired target location. In many cases, the guidewires path through the vascular system will be tortuous, requiring the guidewire to change direction many times. By pushing and rotating the proximal end of the guidewire outside of the patient, the physician is able to direct the distal end of the guidewire to the desired target site. Once the distal portion of the guidewire is proximate the desired location, the catheter may be threaded onto the guidewire and urged distally until the distal end of the catheter is proximate the target location. The catheter often has been unpackaged and prepared for use prior to this point. After being prepared, but prior to actual use, the catheter must be laid out and kept sterile without being put back in the original package. It is often useful to be able to coil the catheter in order to facilitate handling and save space either laying out or hanging up the catheter, because of the length of the catheter (typically over 1 meter long).

Typically, the catheter enters the patient's vasculature at a convenient location such as a blood vessel in the neck or near the groin. Once the distal portion of the catheter has entered the patient's vascular system, the physician may urge the distal tip forward by applying longitudinal forces to the proximal portion of the catheter. In order for the catheter to effectively communicate these longitudinal forces and resist kinking, the proximal portion of many intravascular catheters is made relatively stiff.

The path taken by a catheter through the vascular system is often tortuous, requiring the catheter to change direction frequently. In some cases, it may even be necessary for the catheter to double back on itself. In order for the catheter to conform to a patient's tortuous vascular system, the distal portion of many intravascular catheters is very flexible or floppy.

The distance between the access site and the target site is often in excess of 100 cm. In order to assure that the physician will have access to the proximal end of the catheter when the distal end of the catheter is disposed near the target site, many intravascular catheters are relatively long. For example, a catheter shaft may have a length from about 70 cm to about 150 cm.

While the distal end of an intravascular catheter is being advanced into the body of a patient, a proximal portion of the catheter extends outside the body of the patient. During this procedure, care must be taken to assure that the proximal portion of the catheter remains inside the sterile field. If the proximal portion of the catheter were allowed to touch a non-sterile surface (e.g., the floor), the contaminated intravascular catheter would need to be discarded and replaced. The discarding of a contaminated intravascular catheter and replacing it with a new, sterile one adds expense to the surgical procedure. More critically, the replacement procedure adds time to the procedure. In some cases, the duration of the procedure may be substantially extended. For example, a dilation catheter may need to be "prepped" before it is used. This preparation procedure may include the time consuming steps of evacuating air from the device and back filling the device with a fluid. A longer procedure is inherently more expensive; but more importantly, a longer procedure may present a greater risk to the patient.

Intravascular catheters may be utilized for various diagnostic and/or therapeutic purposes. One example of a therapeutic use for an intravascular catheter is percutaneous transluminal angioplasty (PTA). An angioplasty procedure typically involves the use of a dilation catheter. The dilation catheter is typically advanced through the vasculature of a patient until a balloon portion of the dilation catheter is positioned proximate the restriction in the diseased vessel. The balloon is then inflated, and the restriction in the vessel is opened. In some cases, multiple restrictions may be opened utilizing a single dilation catheter. When this is the case, the dilation catheter may be partially or completely withdrawn from the body of the patient. When the catheter is withdrawn, care must be taken to assure that the catheter remains inside the sterile field.

As described above, the proximal portion of many intravascular catheters is quite stiff. Because the distal portion of these catheters is typically stiff, intravascular catheters are biased to assume a straight shape and will not readily remain in a coiled configuration. In some cases, it is necessary for an assistant to hold the proximal portion of the catheter while it is being introduced or withdrawn from a patient. The assistant may manually coil the proximal portion of the intravascular catheter and hold it in a coiled configuration. The addition of an assistant to the surgical environment to hold the catheter proximal portion is quite costly. The physicians and other personnel involved in a surgical procedure also must wear surgical gloves for the duration of the procedure. In many cases, a "double-gloving" procedure is used. The wearing of surgical gloves inhibits the surgeon's ability to manipulate small objects.

SUMMARY OF THE INVENTION

The present invention relates generally to catheters for performing medical procedures. More particularly, the present invention relates to methods and devices for managing a portion of the catheter which is extending from the body of the patient under operating room conditions (e.g., a sterile field while the physician is wearing surgical gloves). Methods and devices in accordance with the present invention may also be utilized to manage a shaft of the catheter after the catheter is unpacked, but prior to use in a surgical procedure.

A catheter in accordance with one embodiment of the present invention includes a catheter shaft having a proximal end and a distal end, and a keeper fixed to the catheter proximate the proximal end thereof. The keeper includes one or more inside surfaces defining a channel which is adapted to entrap a straight portion of the catheter shaft. The keeper also includes a passageway which is adapted to allow a portion of the catheter shaft which has been urged into a curved shape to pass into the channel of the keeper.

In one method in accordance with the present invention, the catheter shaft may be urged into a curved shape by exerting one or more pushing forces on the catheter shaft. For example, a physician may push on the catheter shaft with a gloved thumb. In another method in accordance with the present invention, a loop may be formed with the catheter shaft. In this method, a portion of the loop may be passed through the passageway and into the channel of the keeper. This embodiment of the present invention enables the physician to capture a portion of the shaft within the keeper without manipulating or deforming the keeper. An advantage of this method is that a physician is able to perform the required steps easily, even while wearing two pairs of surgical gloves.

A catheter in accordance with an additional embodiment of the present invention includes a catheter shaft having a proximal end and a distal end, and a keeper fixed to the catheter proximate a proximal end thereof. The keeper includes a first arm and a second arm defining an aperture. In one method in accordance with the present invention, the catheter shaft is placed in a first position between the first arm and the second arm. The catheter shaft may be twisted and moved to a second position within the aperture defined by the first arm and the second arm. Preferably, the first arm and the second arm releasably trap the catheter shaft when it is disposed within the aperture of the keeper. It should be noted that a physician may position the catheter shaft in the first position and the second position without manipulating the keeper directly. For example, a physician may grasp a hub of the catheter in one hand and a portion of the catheter shaft in a second hand. The catheter shaft has sufficient length that it may be grasped between the palm and fingers of a hand. The keeper of this embodiment allows a physician to capture a portion of the catheter shaft easily, even when wearing two pairs of surgical gloves.

A catheter in accordance with yet another embodiment of the present invention includes a catheter shaft having a proximal end and a distal end. The catheter also includes a hub and a keeper which is fixed to the hub. In a preferred embodiment, the keeper is adapted to clip onto the hub. An advantage of this embodiment is that the keeper can be used in conjunction with existing catheters with no modification to the hub. Embodiments of the catheter have also been envisioned in which the keeper and the hub are formed from the same material, for example, by injection molding. The keeper includes one or more tabs. A portion of the catheter shaft may be urged between the tab and the hub.

BRIEF DESCRIPTION OF THE DRAWINGS

FIG. 9 is a plan view of a proximal portion of a catheter having a keeper in accordance with the present invention;

FIG. 10 is a cross-sectional view of the catheter of FIG. 9;

DETAILED DESCRIPTION OF THE INVENTION

The following detailed description should be read with reference to the drawings, in which like elements in different drawings are numbered in like fashion. The drawings, which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
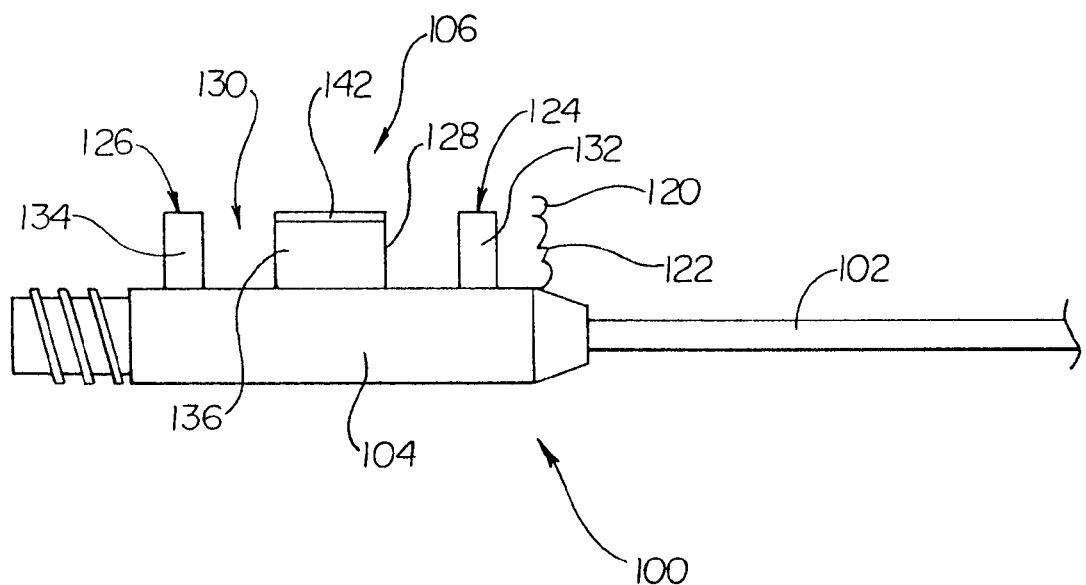
FIG. 1 is a plan view of a proximal portion of a catheter having a keeper in accordance with the present invention.

FIG. 1 is a plan view of a proximal portion of a catheter 100. Catheter 100 includes a catheter shaft 102. A hub 104 is disposed about a proximal end of catheter shaft 102. In order to facilitate the handling of catheter 100, catheter shaft 102 may be wound into a coiled configuration. In a preferred embodiment, catheter shaft 102 is resilient. When catheter shaft 102 is wound into a coiled configuration, catheter shaft 102 is biased to return to a substantially straight shape. Catheter 100 includes a keeper 106 which is adapted to secure catheter shaft 102 in a coiled configuration.

Keeper 106 includes an entrance portion 120 and a capturing portion 122. Keeper 106 includes a first wall 124, a second wall 126, and an opening 130 disposed between first wall 124 and second wall 126. In a preferred embodiment, opening 130 is adapted to accept a portion of catheter shaft 102 which has been urged into a curved shape. First wall 124 defines a first surface 132, and second wall 126 defines a second surface 134.

Keeper 106 also includes a third wall 128. Third wall 128 defines a third surface 136 facing opening 130 of keeper 106. Keeper 106 also includes a projection 142 extending beyond third surface 136 defined by third wall 128. In the embodiment of FIG. 1, projection 142 extends in the general direction of opening 130.

Figure 2:
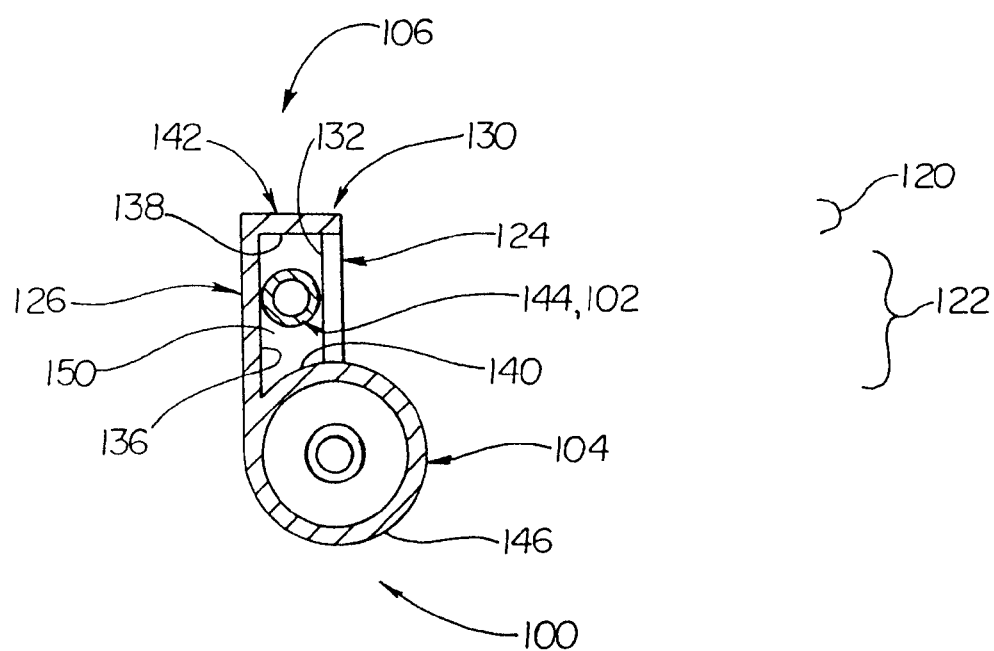
FIG. 2 is a cross-sectional view of the catheter of FIG. 1.

FIG. 2 is a cross-sectional view of catheter 100 of FIG. 1. In FIG. 2, it may be seen that projection 142 extends into opening 130 of keeper 106 and that projection 142 defines a fourth surface 138. In the embodiment of FIG. 2, a captured portion 144 of catheter shaft 102 is disposed between first surface 132 defined by first wall 124 and third surface 136 defined by third wall 128. In FIG. 2, it may be appreciated that keeper 106 includes a fifth surface 140 extending between third surface 136 and first surface 132 defined by first wall 124. In the embodiment of FIG. 2, fifth surface 140 comprises a portion of an outer surface 146 of hub 104.

In the embodiment of FIG. 2, captured portion 144 of catheter shaft 102 is disposed between fourth surface 138 and fifth surface 140. In the embodiment of FIG. 1 and FIG. 2, first surface 132, second surface 134, third surface 136, fourth surface 138, and fifth surface 140 define a channel 150. In a preferred embodiment, channel 150 of keeper 106 is adapted to accept catheter shaft 102. Entrance portion 120 and capturing portion 122 of keeper 106 are also shown in FIG. 2.

Figure 3:
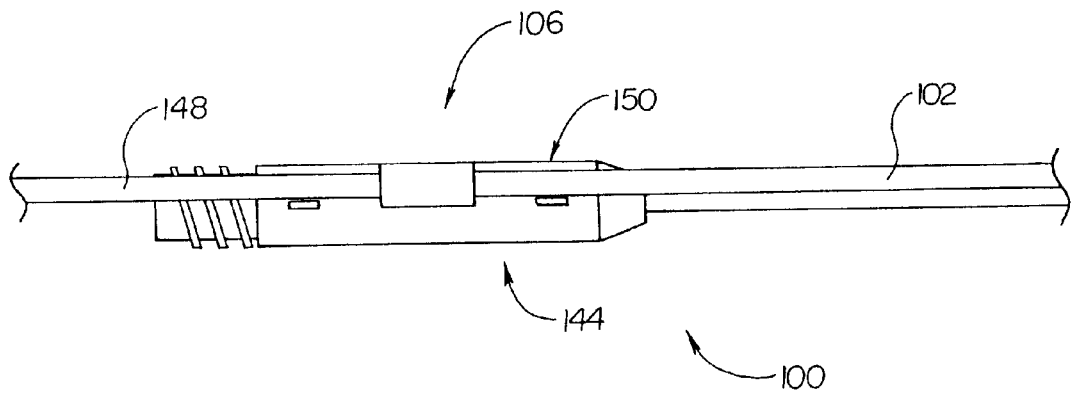
FIG. 3 is a plan view of the catheter of FIG. 1 and FIG. 2.

FIG. 3 is a plan view of catheter 100 of FIG. 1 and FIG. 2. As in the embodiment of FIG. 2, a captured portion 144 of catheter shaft 102 is disposed within channel 150 of keeper 106. In the embodiment of FIG. 3, catheter shaft 102 is disposed in a coiled configuration including a loop 148. In the embodiment of FIG. 3, a plane defined by loop 148 is generally orthogonal to the plane of FIG. 3. As mentioned previously, in a preferred embodiment, catheter shaft 102 is resilient and biased to assume a substantially straight configuration. Catheter shaft 102 may be urged into a curved configuration to aid in positioning captured portion 144 of catheter shaft 102 within channel 150 of keeper 106.

Figure 4:
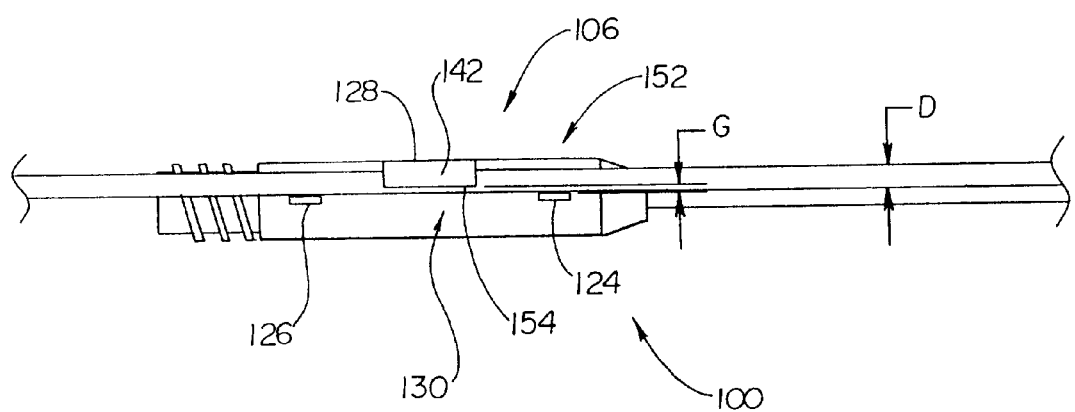
FIG. 4 is a plan view of an additional embodiment of a catheter having a keeper in accordance with the present invention.

FIG. 4 is a plan view of an additional embodiment of catheter 100. As in the previous embodiment, catheter 100 includes a keeper 106 comprising a first wall 124, a second wall 126, and an opening 130 therebetween. Keeper 106 also includes a third wall 128 and a projection 142 extending from third wall 128 towards opening 130. In the embodiment of FIG. 4, there is a gap 152 between an end 154 of projection 142 and a plane extending between first wall 124 and second wall 126. Gap 152 has a width of G. Catheter shaft 102 of catheter 100 has a diameter of D. In a preferred embodiment of catheter 100, the diameter of catheter shaft 102 is greater than the width of gap 152.

Figure 5:
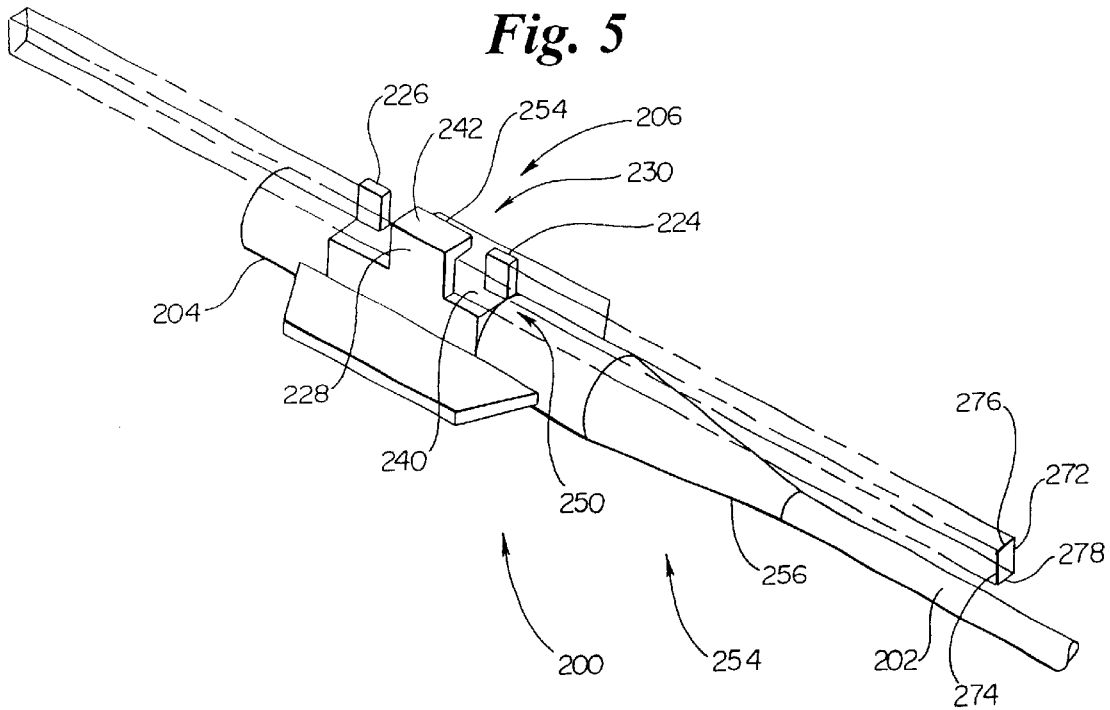
FIG. 5 is a perspective view of an additional embodiment of a catheter having a keeper in accordance with the present invention.

FIG. 5 is a perspective view of an additional embodiment of a catheter 200 in accordance with the present invention. Catheter 200 includes a catheter shaft 202 and a hub 204 disposed about a proximal end 254 of catheter shaft 202. A strain relief 256 is disposed about catheter shaft 202 proximate hub 204. In the embodiment of FIG. 5, a keeper 206 is fixed to hub 204 of catheter 200.

Keeper 206 includes a first wall 224, a second wall 226, and an opening 230 disposed between first wall 224 and second wall 226. First wall 224 and second wall 226 define a first plane 272. Keeper 206 also includes a third wall 228 defining a second plane 274. A projection 242 extends beyond third wall 228 in the general direction of opening 230. Projection 242 defines a third plane 276. In the embodiment of FIG. 5, an end 254 of projection 242 is generally aligned with first plane 272.

Keeper 206 includes a fifth surface 240 extending between first plane 272 and second plane 274. Fifth surface 240 defines a forth plane 278. First plane 272, second plane 274, third plane 276, and forth plane 278 define a channel 250. In a preferred embodiment, channel 250 of keeper 206 is adapted to accept a portion of catheter shaft 202. In the embodiment of FIG. 5, channel 250 has a generally polyhedral shape.

Figure 6:
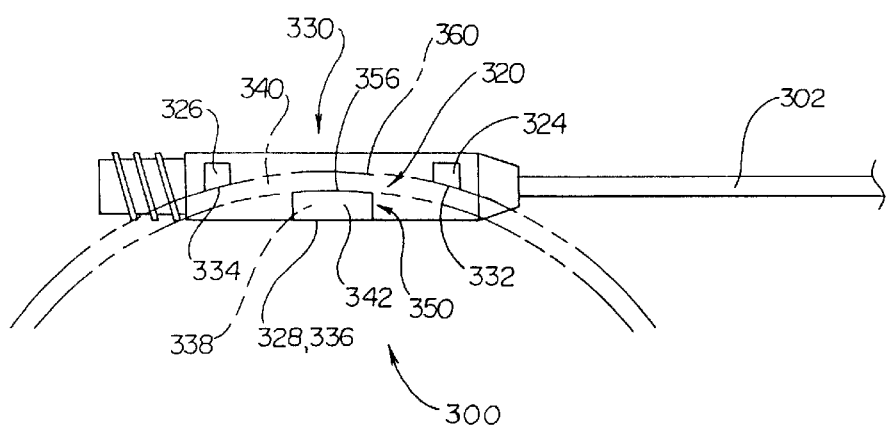
FIG. 6 is a plan view of a proximal portion of a catheter having a keeper in accordance with the present invention.

FIG. 6 is a plan view of an additional embodiment of a catheter 300 in accordance with the present invention. Catheter 300 includes a keeper 306 which is adapted to entrap a portion of a catheter shaft 302 of catheter 300. Keeper 306 includes a first wall 324, a second wall 326, and an opening 330 disposed between first wall 324 and second wall 326. First wall 324 defines a first surface 332 and second wall 326 defines a second surface 334. Keeper 306 also includes a third wall 328 and a projection 342 extending beyond a third surface 336 defined by third wall 328. In the embodiment of FIG. 6, projection 342 extends in the general direction of opening 330. Projection 342 defines a fourth surface 338 and an end surface 358. A fifth surface 340 extends between third wall 328 and first wall 324. In a preferred embodiment of catheter 300, first surface 332, second surface 334, third surface 336, fourth surface 338, and fifth surface 340 define a channel 350 which is adapted to entrap a portion of catheter shaft 302.

In the embodiment of FIG. 6, keeper 306 includes an entrance portion 320 including a passageway 360. As shown in FIG. 6, passageway 360 is defined by first surface 332 of first wall 324, second surface 334 of second wall 326, and end surface 358 of projection 342. In a preferred embodiment, passageway 360 is adapted to accept a portion of catheter shaft 302 which has been urged into a curved shape. Also in a preferred embodiment, a portion of catheter shaft 302 may pass through passageway 360 into channel 350.

Figure 7:
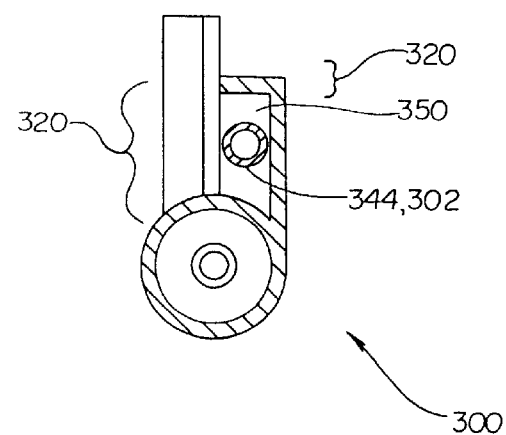
FIG. 7 is a cross-sectional view of the catheter of FIG. 6.

FIG. 7 is a cross-sectional view of catheter 300 of FIG. 6. In the embodiment of FIG. 7, a captured portion 344 of catheter shaft 302 is disposed within channel 350 of keeper 306. In FIG. 7, it may be appreciated that keeper 306 includes an entrance portion 320 including a passageway 360, and a capturing portion 322 including channel 350.

Figure 8:
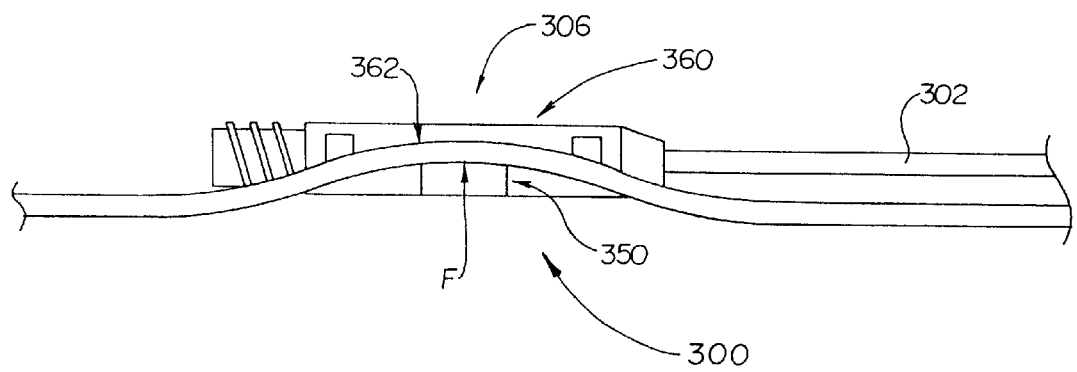
FIG. 8 is a plan view of the catheter of FIG. 6 and FIG. 7, in which a shaft of the catheter has been urged into a curved shape.

FIG. 8 is a plan view of an additional embodiment of catheter 300 of FIG. 6 and FIG. 7. In the embodiment of FIG. 8, a portion of catheter shaft 302 has been positioned proximate passageway 360 of keeper 306. A force F has been applied to catheter shaft 302 forming a curved portion 362 of catheter shaft 302. Force F may be applied to catheter shaft 302, for example, by pushing on catheter shaft 302 with a gloved thumb. In a method in accordance with the present invention, curved portion 362 of catheter shaft 302 may pass through passageway 360 of entrance portion 320 into channel 350 of capturing portion 322.

FIG. 9 is a plan view of an additional embodiment of a catheter 400 having a catheter shaft 402. Catheter 400 includes a keeper 406 having a passageway 460. In the embodiment of FIG. 9, passageway 460 comprises an arcuate slot 464.

FIG. 10 is a cross-sectional view of catheter 400 of FIG. 9. In FIG. 10, it may be appreciated that keeper 406 comprises a first wall 424 having an inside surface 466. Inside surface 466 of first wall 424 defines a channel 450. In the embodiment of FIG. 9 and FIG. 10, channel 450 is generally cylindrical in shape. In FIG. 10, it may also be appreciated that arcuate slot 464 of passageway 460 is defined by first wall 424. In a preferred embodiment of FIG. 10, passageway 460 is adapted to allow a portion of catheter shaft 402 to pass through passageway 460 while it is urged into a curved shape. Once catheter shaft 402 is disposed within channel 450, it may be allowed to return to a straight shape.

Figure 11:
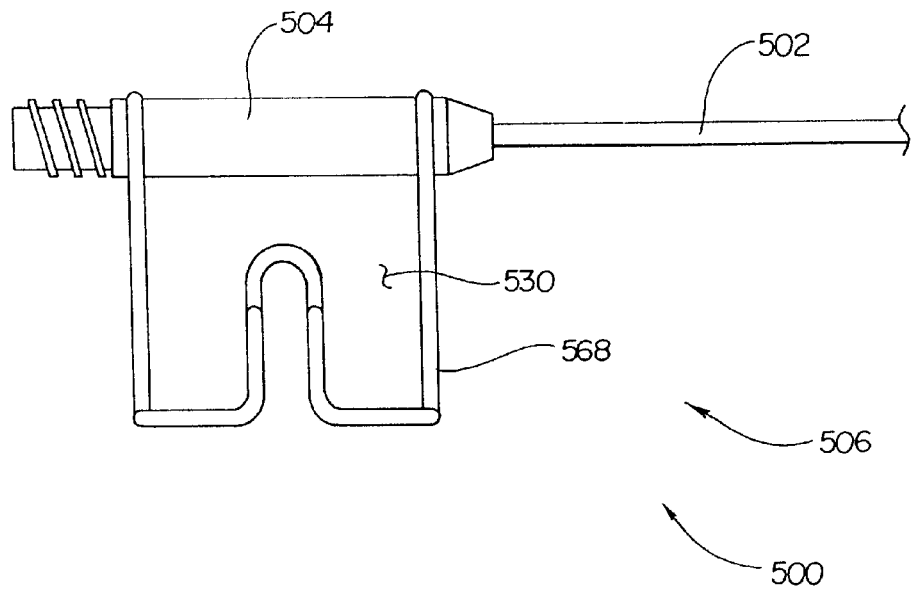
FIG. 11 is a plan view of a proximal portion of a catheter having a keeper in accordance with the present invention.

FIG. 11 is a plan view of an additional embodiment of a catheter 500 in accordance with an additional embodiment of the present invention. Catheter 500 includes a catheter shaft 502, a hub 504, and a keeper 506. In the embodiment of FIG. 11, keeper 506 is fixed to hub 504. Embodiments of the present invention have been envisioned in which keeper 506 is fixed to other portions of a catheter. Examples of portions of a catheter include the catheter shaft and a catheter strain relief. Keeper 506 comprises a keeper member 568 defining an opening 530.

Figure 12:
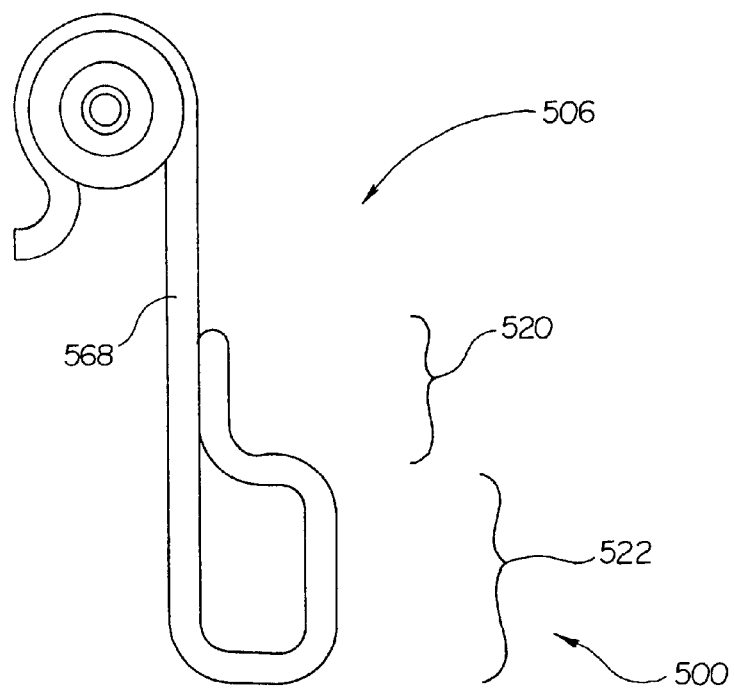
FIG. 12 is an additional plan view of the catheter of FIG. 11.

FIG. 12 is an additional plan view of catheter 500 of FIG. 11. In FIG. 12, it may be appreciated that keeper member 568 of keeper 506 forms an entrance portion 520 and a capturing portion 522 of keeper 506.

Figure 13:
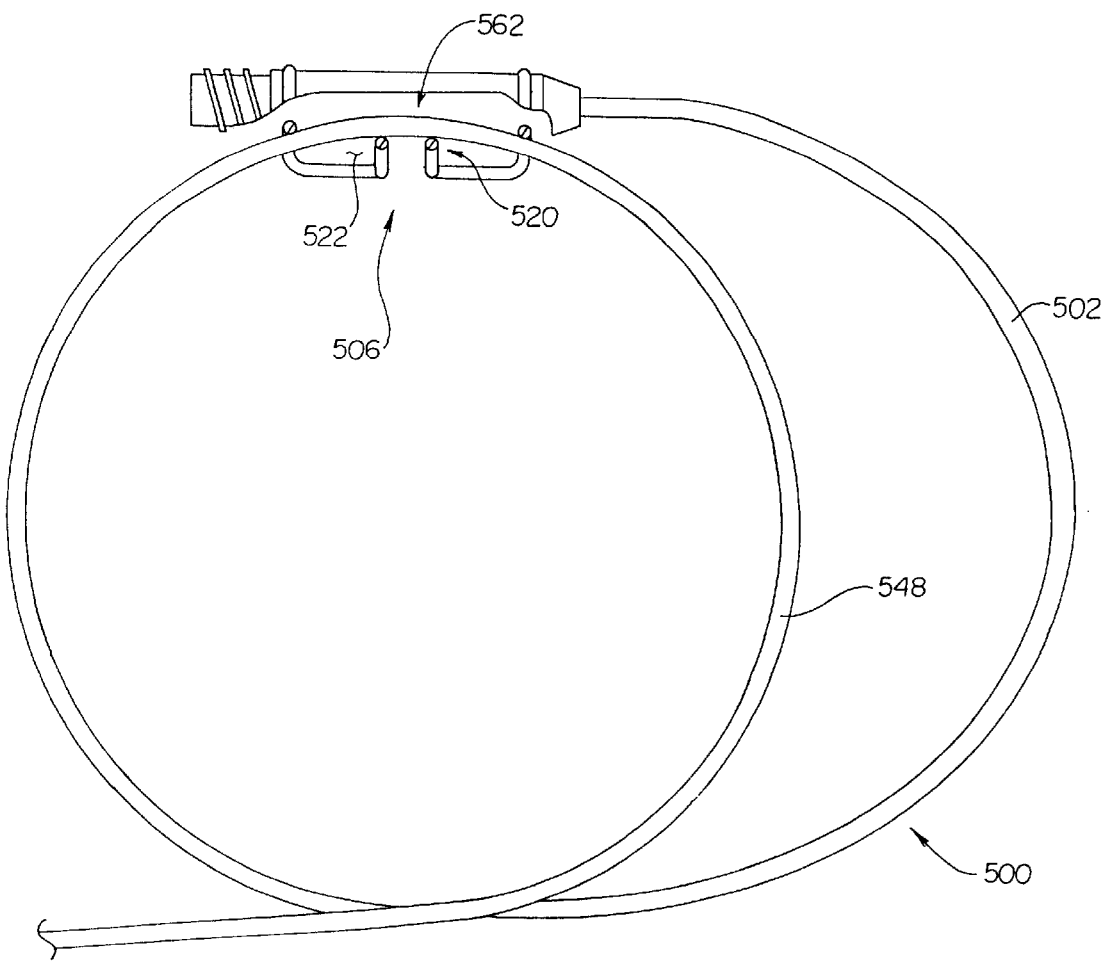
FIG. 13 is an additional plan view of the catheter of FIG. 1 and FIG. 12, in which a portion of the catheter is cut away to illustrate that a loop formed from the catheter shaft may readily pass through an entrance portion of the keeper.

FIG. 13 is a plan view of an additional embodiment of catheter 500 of FIG. 11 and FIG. 12. In the embodiment of FIG. 13, catheter 500 includes a first loop 548 formed from catheter shaft 502. First loop 548 may be held in a general coiled shape by the double-gloved hand of a physician (not shown). In FIG. 13, it may be appreciated that a curved portion 562 of first loop 548 may pass through entrance portion 520 of keeper 506 into capturing portion 522 of keeper 506. It should be noted that a physician may position catheter shaft 502 within capturing portion 522 of keeper 506 without manipulating or deflecting keeper 506. For example, a physician may grasp a proximal portion of catheter 500 in one hand and first loop 548 in a second hand. Once first loop 548 is disposed within capturing portion 522 of keeper 506 it may be rotated to the position shown in FIG. 14.

Figure 14:
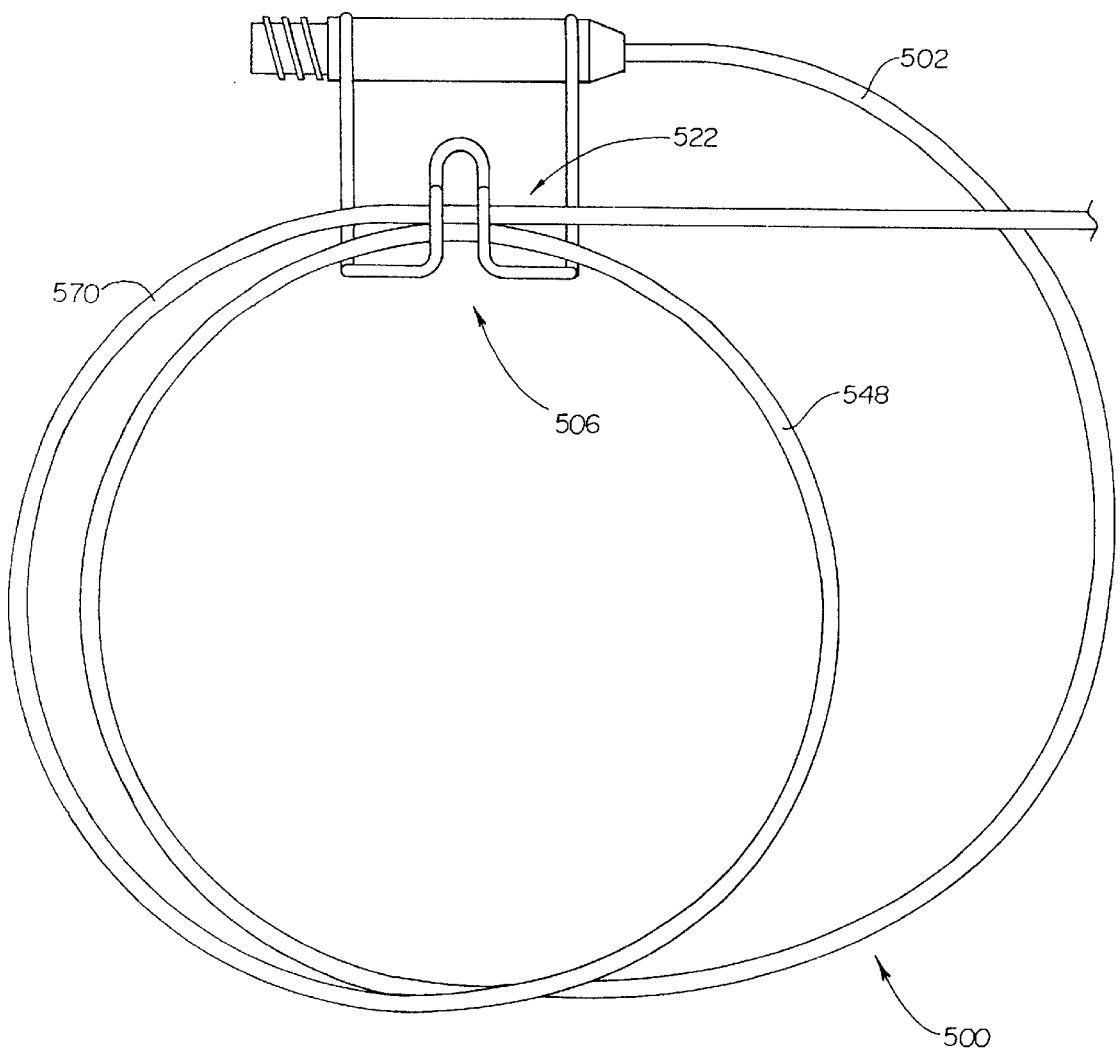
FIG. 14 is an additional plan view of the catheter of FIG. 11, FIG. 12, and FIG. 13, in which a plurality of turns formed by the catheter shaft are trapped by the keeper.

FIG. 14 is a plan view of an additional embodiment of catheter 500 of FIG. 11, FIG. 12, and FIG. 13. The plane of FIG. 14 is generally orthogonal to the plane of FIG. 13. In the embodiment of FIG. 14, a first loop 548 and a second loop 570 formed from catheter shaft 502 are disposed within capturing portion 522 of keeper 506.

Figure 15:
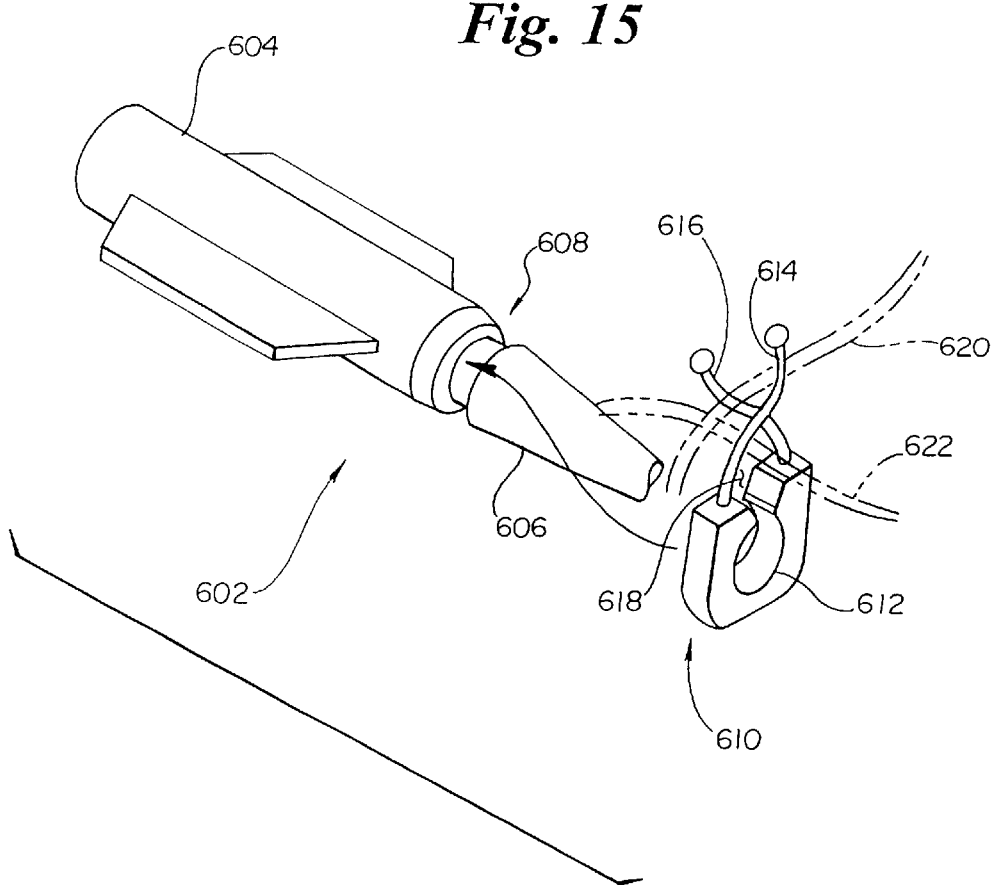
FIG. 15 is a perspective view of an additional embodiment of a catheter having a keeper in accordance with the present invention.

FIG. 15 is a perspective view of an additional embodiment of a catheter 602 in accordance with the present invention. Catheter 602 includes a hub 604 and a strain relief 606. Strain relief 606 defines a groove 608. Catheter 602 also includes a keeper 610 having a groove engaging portion 612 Which is adapted to be disposed in groove 608 of strain relief 606. Keeper 610 includes a first arm 614 and a second arm 616. Keeper 610 also includes an aperture 618 defined by first arm 614 and second arm 616.

In one method in accordance with the present invention, a catheter shaft 600 (shown with phantom lines) of catheter 602 is placed in a first position 620 between first arm 614 and second arm 616. Catheter shaft 600 may be twisted and moved to a second position 622 shown in FIG. 15. When catheter shaft 600 is in second position 622, it is disposed within aperture 618 of keeper 610. In a preferred embodiment, first arm 614 and second arm 616 releasably trap catheter shaft 600 when it is disposed within aperture 618.

It should be noted that a physician may position catheter shaft 600 in first position 620 and second position 622 without manipulating keeper 610 directly. For example, a physician may grasp hub 604 in one hand and catheter shaft 600 in a second hand. Catheter shaft 600 has sufficient length that it may be grasped between the palm and fingers of a hand. Keeper 610 allows a physician to capture a portion of catheter shaft 600 easily, even when wearing two pairs of surgical gloves.

Figure 16:
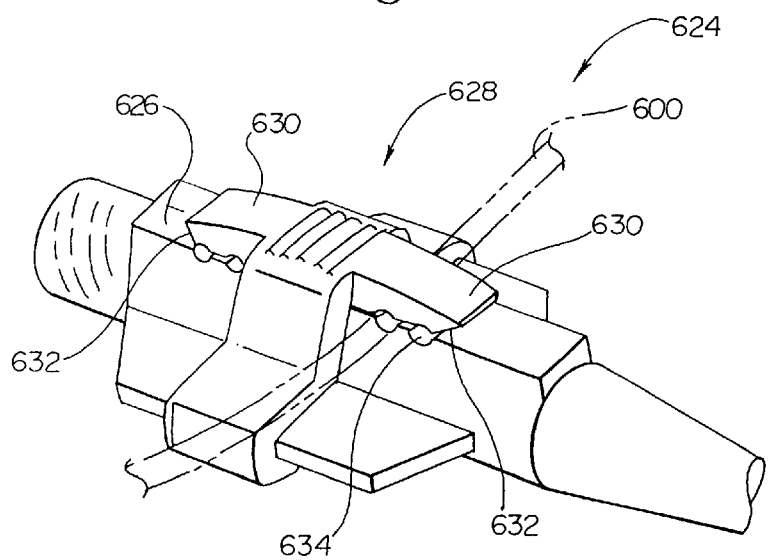
FIG. 16 is a perspective view of an additional embodiment of a catheter having a keeper in accordance with the present invention.

FIG. 16 is a perspective view of an additional embodiment of a catheter 624 in accordance with the present invention. Catheter 624 includes a hub 626 and keeper 628 which is fixed to hub 626. In a preferred embodiment, keeper 628 is adapted to clip onto hub 626. An advantage of this embodiment is that keeper 628 can be used in conjunction with existing catheters with no modification to the hub. Embodiments of catheter 624 have also been envisioned in which keeper 628 and hub 626 are formed from the same material, for example, by injection molding.

Keeper 628 includes a plurality of tabs 630. In the embodiment of FIG. 16, each tab 630 includes a ramp surface 632. A catheter shaft 600 (shown with phantom lines) of catheter 624 may be urged between a tab 630 and hub 626. It should be noted that a physician may position catheter shaft 600 between tab 630 and hub 626 without manipulating keeper 628 directly. For example, a physician may grasp hub 626 in one hand and catheter shaft 600 in a second hand. Catheter shaft 600 has sufficient length that it may be grasped between the palm and fingers of a hand. Keeper 628 allows a physician to capture a portion of catheter shaft 600 easily even when wearing two pairs of surgical gloves. In FIG. 16, it may be appreciated that hub 626 and keeper 628 each define a plurality of grooves 634. Catheter shaft 600 (shown with phantom lines) of catheter 624 may be urged into grooves 634. Embodiments of the catheter 624 have been envisioned in which keeper 628 includes grooves 634, and hub 626 does not. Likewise, embodiments of catheter 624 have been envisioned in which hub 626 includes grooves 634, and keeper 628 does not.

In the embodiment of FIG. 16, each tab 630 is generally parallel to a central axis of hub 626. Embodiments of the present invention have been envisioned in which tab 630 are generally orthoginal to a longitudinal axis of hub 626. In this envisioned embodiment the portion of catheter shaft 600, shown in FIG. 16, would run generally parallel to the longitudinal axis of hub 626 rather than crossing over hub 626 as shown in FIG. 16.

Figure 17:
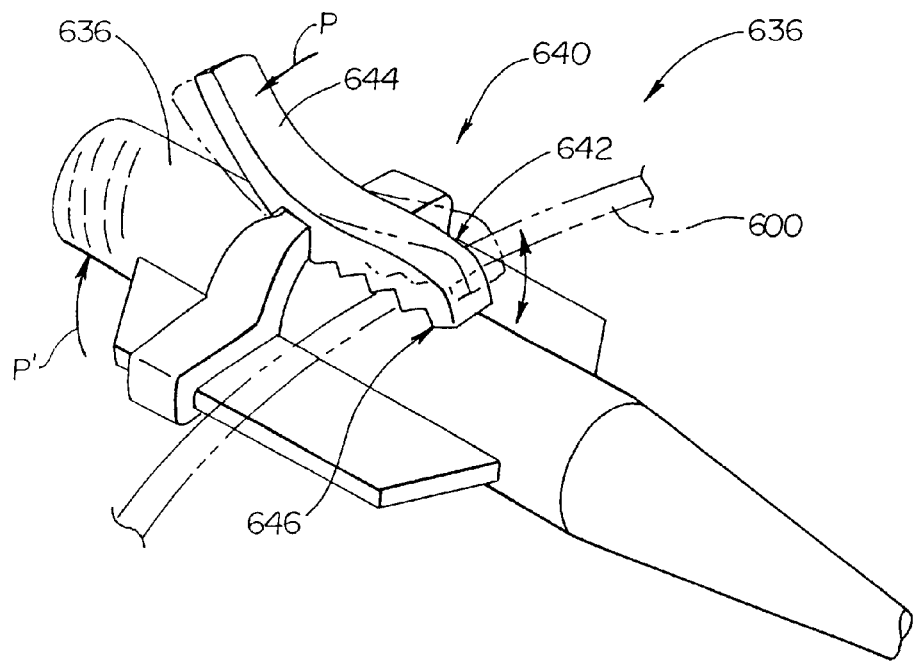
FIG. 17 is a perspective view of an additional embodiment of a catheter having a keeper in accordance with the present invention.

FIG. 17 is a perspective view of an additional embodiment of a catheter 636 in accordance with the present invention. Catheter 636 includes a hub 638 and keeper 640 which is fixed to hub 638. In a preferred embodiment, keeper 640 is adapted to clip onto hub 638. An advantage of this embodiment is that keeper 640 can be used in conjunction with existing catheters with no modification to the hub. Keeper 640 includes a jaw 642 and an ear 644.

A catheter shaft 600 (shown with phantom lines) of catheter 636 may be trapped between jaw 642 and hub 638. In one method in accordance with the present invention, a physician may apply pinching forces P and P' to ear 644 and hub 638, respectively, as shown in FIG. 17. In this exemplary method, the application of forces P and P' will enlarge a gap 646 between jaw 642 and hub 638. When gap 646 is enlarged, catheter shaft 600 may be positioned between jaw 642 and hub 638 with substantially zero insertion force. Once catheter shaft 600 is in the desired position, forces P and P' may be removed, allowing jaw 642 to close onto catheter shaft 600.

In the embodiment of FIG. 16, jaw 642 is disposed generally parallel to a longitudinal axis of hub 638. Embodiments of keeper 640 have been envisioned in which jaw 642 is disposed in an orthogonal arrangement relative to a longitudinal axis of hub 638. In this envisioned embodiment, catheter shaft 600 coils of catheter shaft 600 would be disposed generally parallel to the longitudinal axis of hub 638 rather than crossing over hub 638 as shown in FIG. 17.

Figure 18:
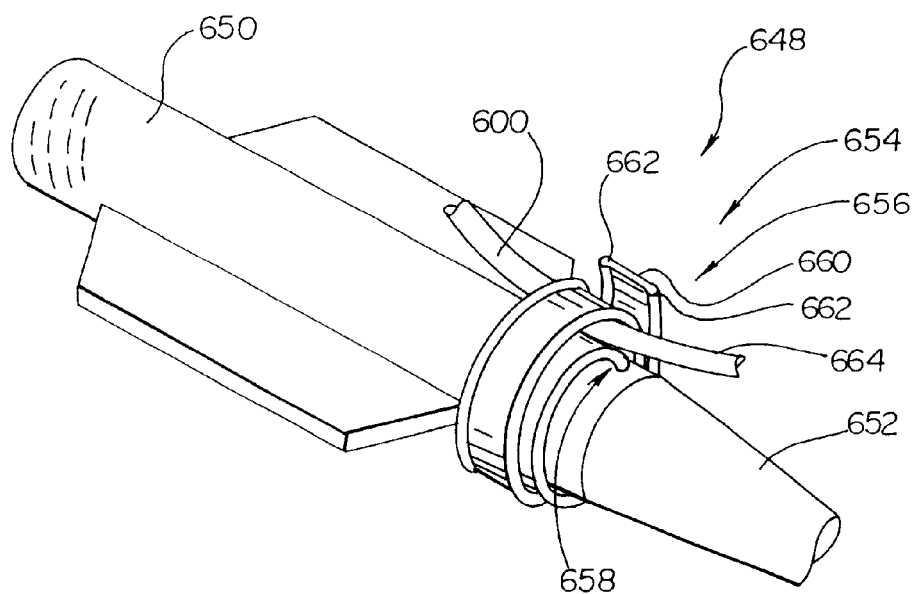
FIG. 18 is a perspective view of an additional embodiment of a catheter having a keeper in accordance with the present invention.

FIG. 18 is a perspective view of an additional embodiment of a catheter 648 in accordance with the present invention. Catheter 648 includes a hub 650, a strain relief 652, and a keeper 654. Keeper 654 comprises a ribbon 656 having a fixed end 658 which is fixed to strain relief 652, for example, by over-molding. In the embodiment of FIG. 18, ribbon 656 comprises a web 660 and a plurality of wires 662.

In one method in accordance with the present invention, a coil 664 may be formed from a catheter shaft 600 of catheter 648. In this method, coil 664 may be positioned proximate strain relief 652 and ribbon 656 of keeper 654 may be wrapped around a portion catheter shaft 600. This method may be utilized by a physician to aid in managing catheter shaft 600 by keeping a portion of catheter shaft 600 in a coiled configuration.

In the embodiment of FIG. 18, a plurality of turns have been formed around hub 650 by ribbon 656. In the embodiment of FIG. 18, the turns of ribbon 656 generally overly one another. Embodiments of keeper 654 have also been envisioned in which the multiple turns of ribbon 656 are longitudinally disposed along the length of hub 650, strain relief 652, and catheter shaft 600. In this envisioned embodiment, multiple wraps of ribbon 656 may serve to hold multiple coils of catheter shaft 600 in a relatively tight bundle.

Figure 19:
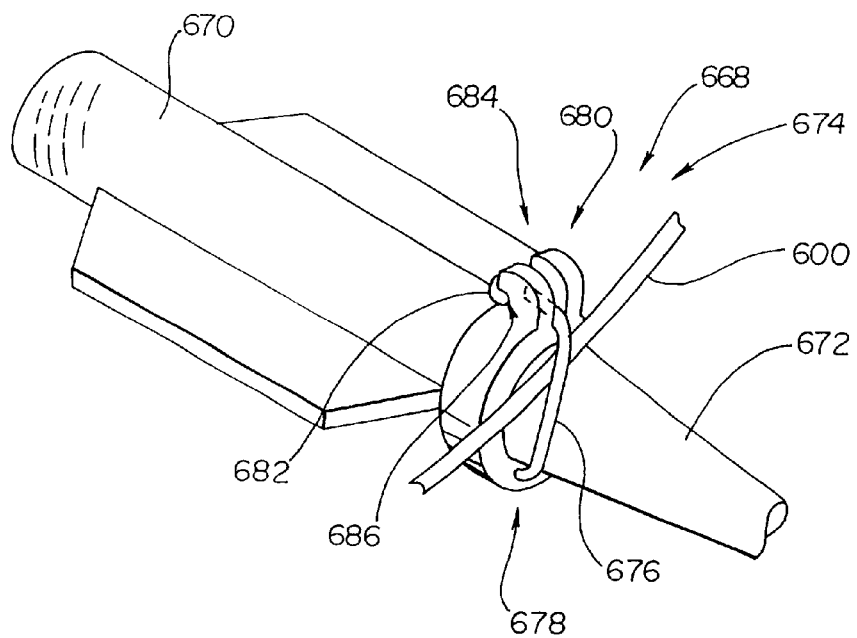
FIG. 19 is a perspective view of an additional embodiment of a catheter having a keeper in accordance with the present invention.

FIG. 19 is a perspective view of an additional embodiment of a catheter 668 in accordance with the present invention. Catheter 668 includes a hub 670, a strain relief 672, and a catheter shaft 600. Catheter 668 also includes a keeper 674 which is fixed to catheter 668 between hub 670 and strain relief 672. Keeper 674 comprises a filament 676 having a fixed end 678 and a free end 680. A radial enlargement or bulbous end 682 is disposed about free end 680 of filament 676 to lock the keeper 674 in a closed position. To allow this to function, keeper 674 also includes a bifurcation 684 which is adapted to receive a portion of bulbous end 682 and filament 676. In a preferred embodiment, filament 676 is comprised of an elastomeric material. Examples of materials which may be suitable in some applications include silicone rubber and thermoplastic elastomer (TPE).

In one method in accordance with the present invention, a portion of catheter shaft 600 may be positioned proximate strain relief 672 and filament 676 may be looped over catheter shaft 600, trapping catheter shaft 600 against strain relief 672. In a preferred method, filament 676 may be stretched and bulbous end 682 may be positioned proximate bifurcation 684. In this preferred method, tension from filament 676 will urge bulbous end 682 into a recess 686 in bifurcation 684.

Embodiments of keeper 674 have been envisioned in which filament 676 makes multiple wraps around strain relief 672, and/or hub 670, and catheter shaft 600. The multiple wraps of filament 676 may be disposed longitudinally along the length of strain relief 672, hub 670, and catheter shaft 600. Disposing multiple wraps of filament 676 longitudinally may serve to retain multiple coils of catheter shaft 600 in a tight bundle.

Figure 20:
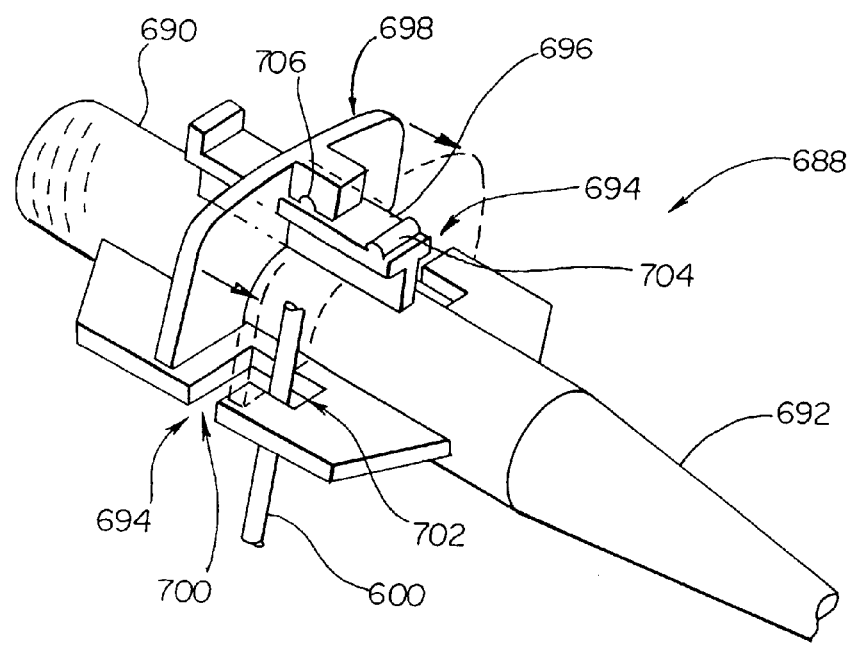
FIG. 20 is a perspective view of an additional embodiment of a catheter having keeper in accordance with the present invention.

FIG. 20 is a perspective view of an additional embodiment of a catheter 688 in accordance with the present invention. Catheter 688 includes a hub 690, a strain relief 692, and a catheter shaft 600. Hub 690 of catheter 688 defines a plurality of slots 694. Hub 690 also forms a slide 696. A gate 698 is disposed in sliding engagement with slide 696 of hub 690.

In the embodiment of FIG. 20, each slot 694 includes an entry portion 700 and a capturing portion 702. Gate 698 is adapted to obstruct entry portion 700 of each slot 694 when it is slid in the direction indicated by the arrows in FIG. 20. Gate 698 defines a groove 706. Slide 696 includes a rib 704 which is adapted to be received within groove 706. In a preferred embodiment, groove 706 and rib 704 cooperate to lock gate 698 in a position which obstructs entry portion 700 of each slot 694.

Figure 21:
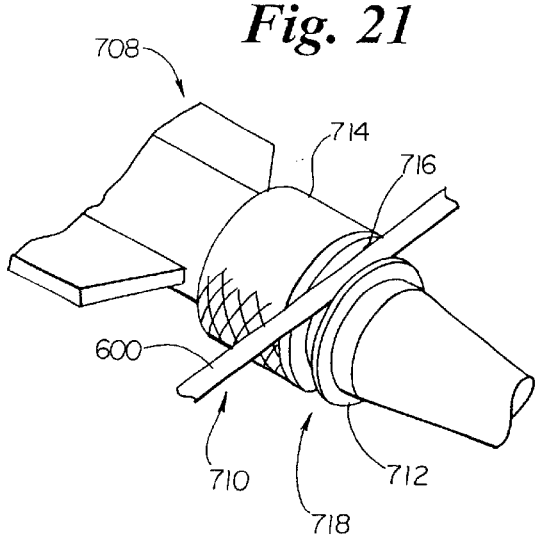
FIG. 21 is a perspective view of an additional embodiment of a catheter having a keeper in accordance with the present invention.

FIG. 21 is a perspective view of an additional embodiment of a catheter 708 having a keeper 710. Keeper 710 includes a flange 712, a ring 714, and a washer 716. As shown in FIG. 21, flange 712 and washer 716 define a slot 718. A portion of a catheter shaft 600 of catheter 708 is disposed within slot 718. In a preferred embodiment, ring 714 is adapted to be urged distally, creating a friction fit between washer 716 and catheter shaft 600.

Figure 22:
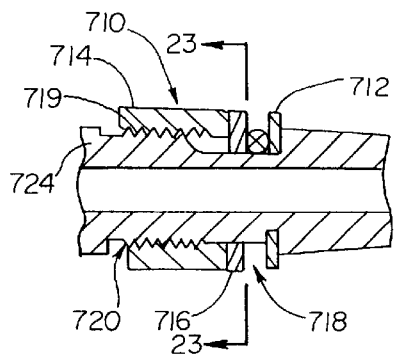
FIG. 22 is a cross-sectional view of the catheter of FIG. 21.

FIG. 22 is a cross-sectional view of keeper 710 of FIG. 21. In FIG. 22, it may be appreciated that ring 714 includes a female thread 719. Female thread 719 of ring 714 engages a male thread 720 defined by hub 724. Ring 714 may be rotated to adjust the width of slot 718 defined by flange 712 and washer 716. Ring 714 may also be utilized to pinch catheter shaft 600 between flange 712 and washer 716.

Figure 23:
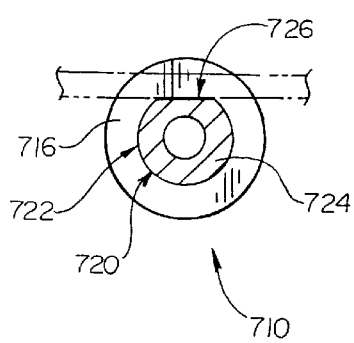
FIG. 23 is a cross-sectional view of the catheter of FIG. 21 and FIG. 22.

FIG. 23 is a cross-sectional view of keeper 710 of FIG. 21 and FIG. 22. In FIG. 23, it may be appreciated that hub 724 includes a flat 726 disposed proximate male thread 720. Washer 716 includes a generally D-shaped hole 722 which is adapted to accept male thread 720 and flat 726 of hub 724. In a preferred embodiment, flat 726 of hub 724 and D-shaped hole 722 of washer 716 cooperate to preclude washer 716 from rotating.

Figure 24:
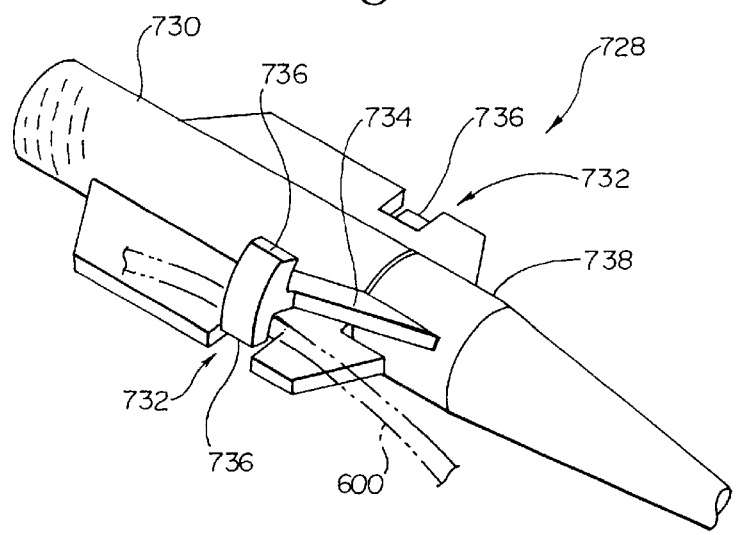
FIG. 24 is a perspective view of an additional embodiment of a catheter having a keeper in accordance with the present invention.

FIG. 24 is a perspective view of an additional embodiment of a catheter 728 in accordance with the present invention. Catheter 728 includes a hub 730 disposed about a proximal portion of a catheter shaft 600 of catheter 728. Hub 730 of catheter 728 defines a plurality of slots 732. A locking member 738 is disposed in pivotal engagement with hub 730. Locking member 738 includes a plurality of wings 734. A plurality of tangs 736 project from each wing. In a method in accordance with the present invention, a portion of catheter shaft 600 may be trapped between hub 730 and a wing 734. In the embodiment of FIG. 24, each slot 732 defined by hub 730 is adapted to accept a tang 736.

Figure 25:
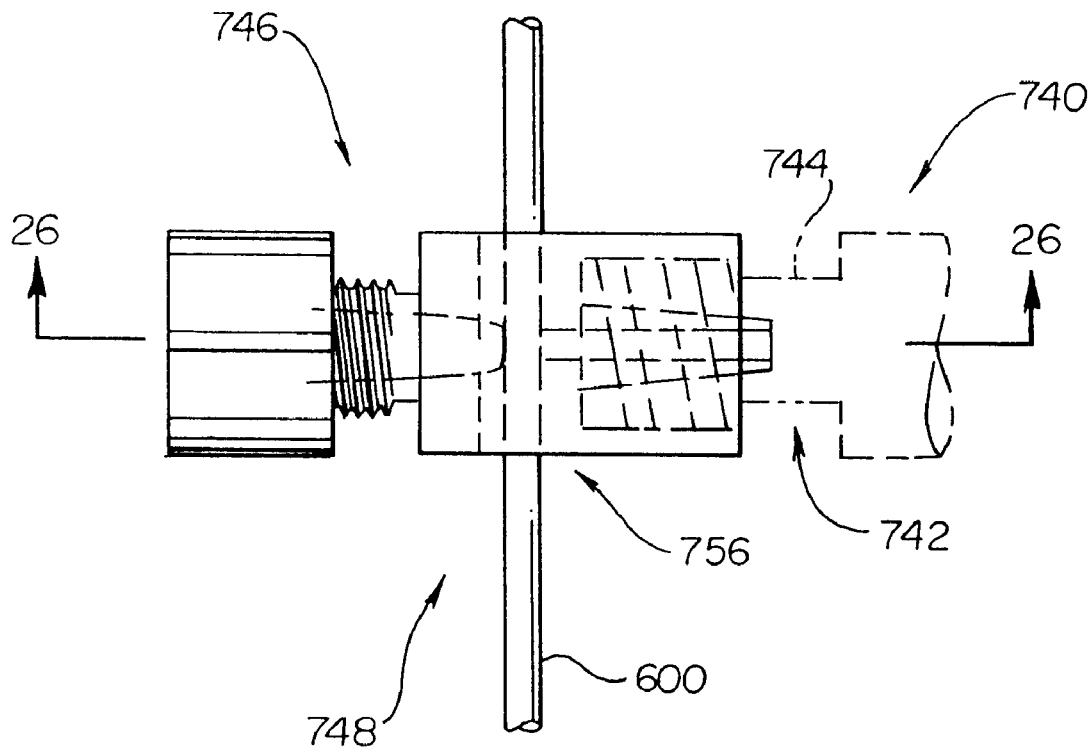
FIG. 25 is a plan view of an additional embodiment of a catheter having a keeper in accordance with the present invention.

FIG. 25 is a perspective view of an additional embodiment of a catheter 740 in accordance with the present invention. Catheter 740 includes a catheter shaft 600 and a port 742. In the embodiment of FIG. 25, a keeper 746 is releasably coupled to port 742 of catheter 740. In a preferred embodiment, port 742 comprises a male luer fitting 744 and keeper 746 includes a female luer fitting 744. Keeper 746 also includes a keeper body 756 defining a lumen 748. In the embodiment of FIG. 25, a portion of catheter shaft 600 is disposed within lumen 748.

Figure 26:
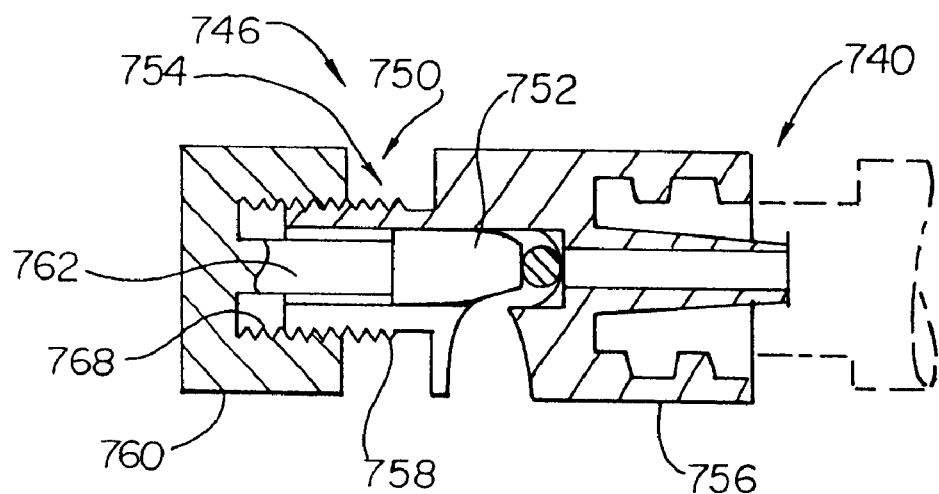
FIG. 26 is a cross-sectional view of the catheter of FIG. 25.

FIG. 26 is a cross-sectional view of catheter 740 of FIG. 25. In FIG. 26, it may be appreciated that keeper 746 includes a catheter fixing mechanism 750. Catheter fixing mechanism 750 includes a jam 752 and a jam motion control 754. Jam motion control 754 includes a male thread 758 defined by keeper body 756 and a female thread 768 defined by a knob 760. A shaft 762 extends between knob 760 and jam 752. Catheter shaft 600 may be fixed within lumen 748 of keeper 746 by rotating knob 760 of jam motion control 754 in a first direction until jam 752 contacts catheter shaft 600. Catheter shaft 600 may be release by rotating knob 760 in a second direction.

Figure 27:
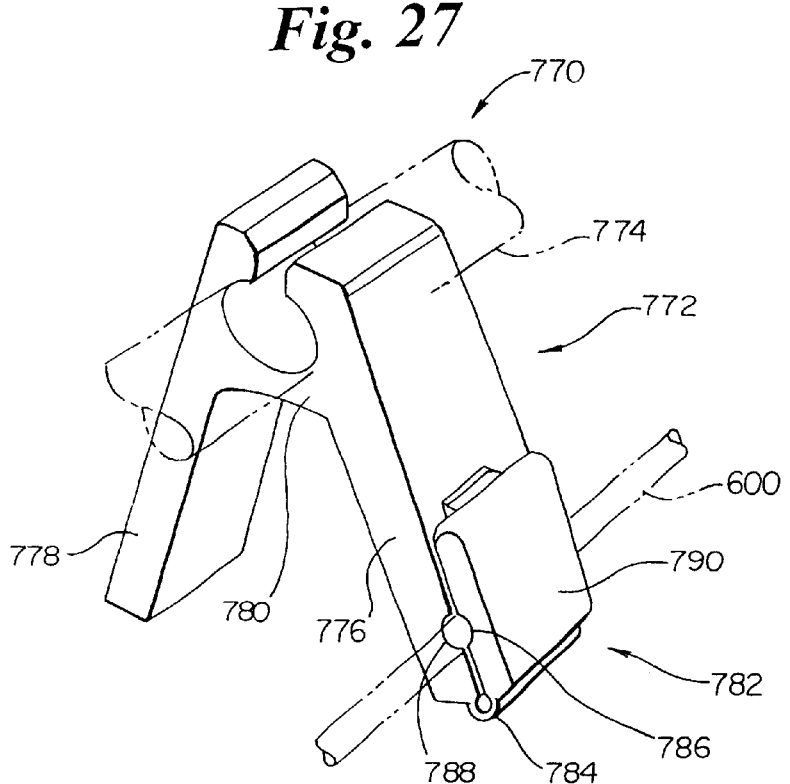
FIG. 27 is a perspective view of an additional embodiment of a keeper in accordance with the present invention.

FIG. 27 is a perspective view of an additional embodiment of a catheter 770 in accordance with the present invention. Catheter 770 includes a catheter shaft 600. A keeper 772 is fixed to a portion 774 of catheter 770. Keeper 772 includes a first leg 776, a second leg 778, and a crotch 780 extending between first leg 776 and second leg 778. Keeper 772 also includes a latch 782 which is adapted to trap a portion of catheter shaft 600. Latch 782 includes a door 790 which is coupled to first leg 776 by a hinge 784. In the embodiment of FIG. 27, door 790 includes a groove 786 and first leg 776 includes a groove 788. A portion of catheter shaft 600 is trapped between door 790 of latch 782 and first leg 776. The position of door 790 in FIG. 27 may be generally referred to as a closed position.

Embodiments of keeper 772 have been envisioned in which door 790 includes a plurality of grooves 786 and first legs 776 includes a plurality of grooves 788. In these envisioned embodiments, keeper 772 may retain a plurality of turns of catheter shaft 600.

Figure 28:
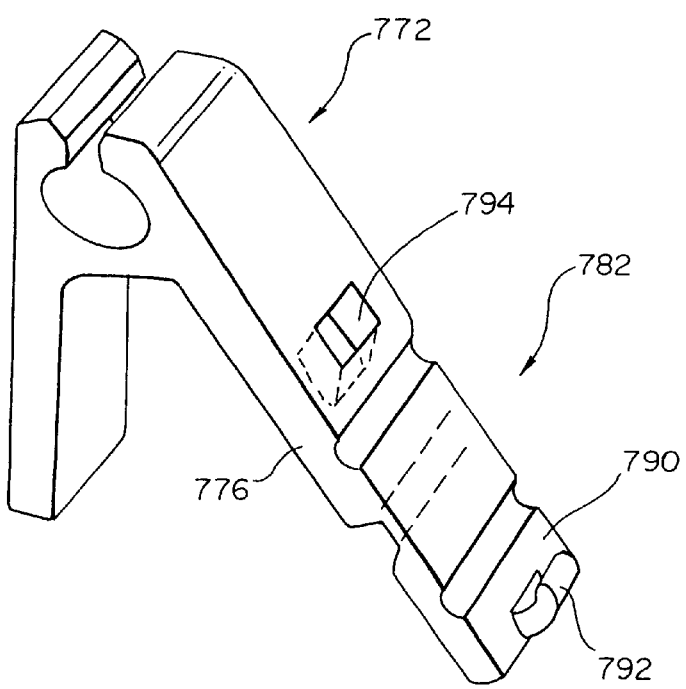
FIG. 28 is a perspective view of the keeper of FIG. 27.

FIG. 28 is a perspective view of an additional embodiment of keeper 772 of FIG. 27. In the embodiment of FIG. 28, door 790 has been moved to an open position. In FIG. 28, it may be appreciated that latch 782 includes a clasp member 792. First leg 776 includes a clasp member receiver 794. In a preferred embodiment, clasp member 792 and clasp member receiver 794 cooperate to releasably hold door 790 in the closed position. In the embodiment of FIG. 28, keeper 772 has been removed from portion 774 of catheter 770. Embodiments of keeper 772 have been envisioned in which keeper 772 is adapted to be fixed to various objects, for example, a table.

Figure 29:
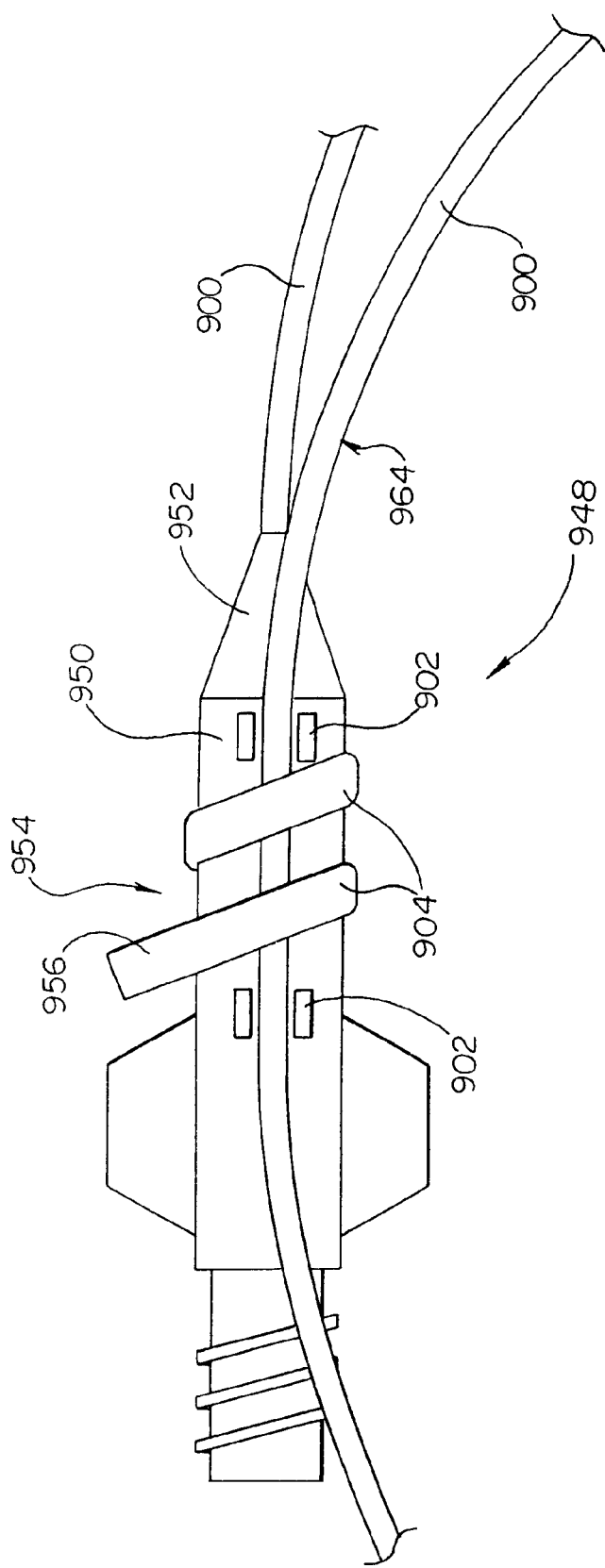
FIG. 29 is a plan view of an additional embodiment of a catheter in accordance with the present invention.

FIG. 29 is a plan view of an additional embodiment of a catheter 948 in accordance with the present invention. Catheter 948 includes a hub 950, a strain relief 952, and a keeper 954. Keeper 954 comprises a ribbon 956 having a fixed end which is fixed to hub 950. A coil 964 is formed from a catheter shaft 900 of catheter 948. In the embodiment of FIG. 29, a portion of coil 964 is disposed between a plurality of projections 902. A plurality of turns 904 of ribbon 956 are disposed about a portion of catheter shaft 900 and a portion of hub 950. Turns 904 of ribbon 956 are longitudinally disposed along the length of hub 950.

Figure 30:
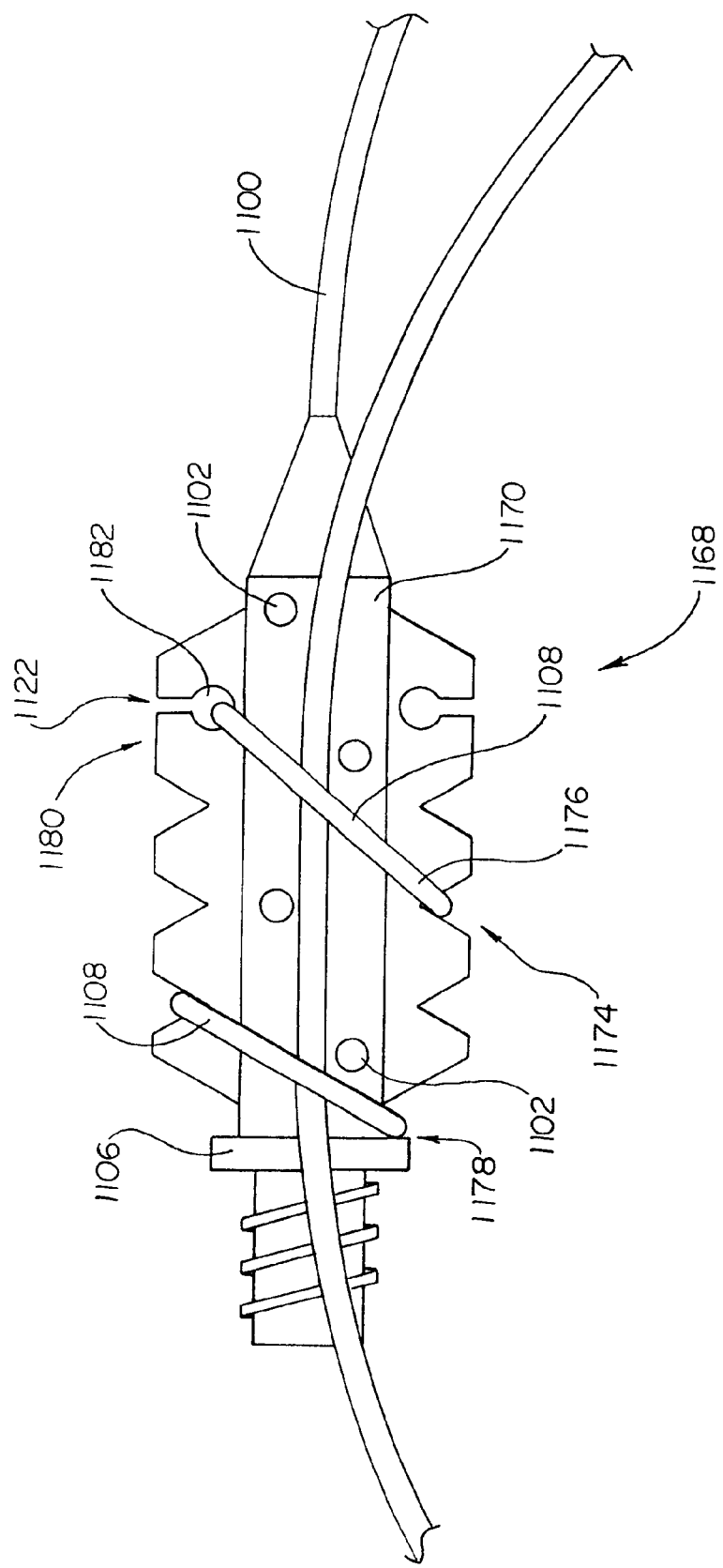
FIG. 30 is a plan view of an additional embodiment of a catheter in accordance with the present invention.

FIG. 30 is a plan view of an additional embodiment of a catheter 1168 in accordance with the present invention. Catheter 1168 includes a catheter shaft 1100 and a hub 1170 having a plurality of projections 1102. In the embodiment of FIG. 30, a portion of catheter shaft 1100 is disposed between a plurality of projections 1102. Catheter 1168 also includes a keeper 1174 comprising a filament 1176 having a fixed end 1178 and a free end 1180. Fixed end 1178 of filament 1176 is fixed to a ring 1106 which is disposed about a portion of hub 1170. A radial enlargement or bulbous end 1182 is disposed about free end 1180 of filament 1176 to lock the keeper 1174 in a closed position. Hub 1170 defines an aperture 1122 which is adapted to receive a portion of bulbous end 1182 and filament 1176. In a preferred embodiment, filament 1176 is comprised of an elastomeric material. Examples of materials which may be suitable in some applications include silicone rubber and thermoplastic elastomer (TPE). A plurality of wraps 1108 of filament 1176 are disposed about a portion of catheter shaft 1100 and a portion of hub 1170. It may be noted in FIG. 30 that wraps 1108 of filament 1176 are longitudinally disposed along the length of hub 1170.

Figure 31:
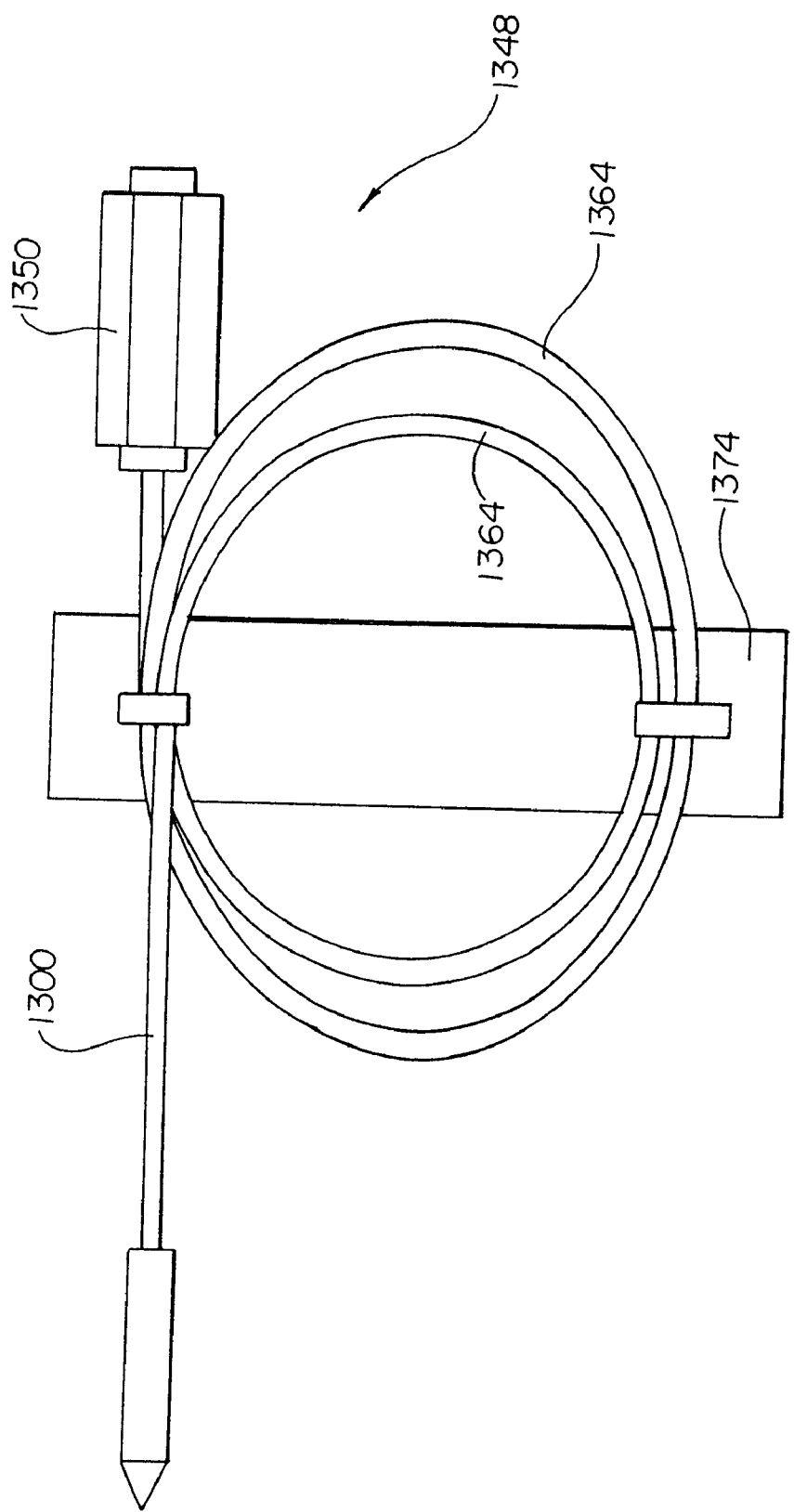
FIG. 31 is a plan view of a catheter and a keeper in accordance with the present invention.

FIG. 31 is a plan view of an additional embodiment of a catheter 1348 in accordance with the present invention. Catheter 1348 includes a hub 1350 and a shaft 1300 forming a plurality of coils 1364. In a preferred embodiment, shaft 1300 of catheter 1348 is held in a coiled configuration by a keeper 1374.

Figure 32:
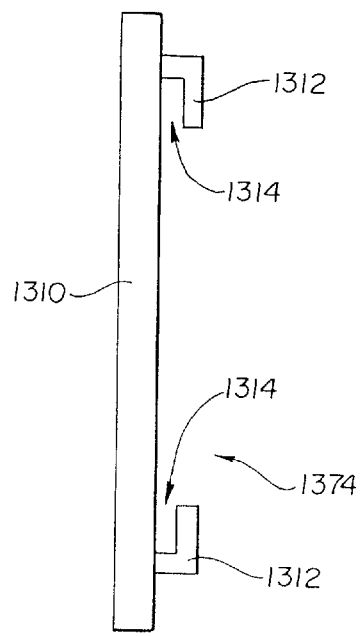
FIG. 32 is a plan view of the keeper of FIG. 31.
Figure 33:
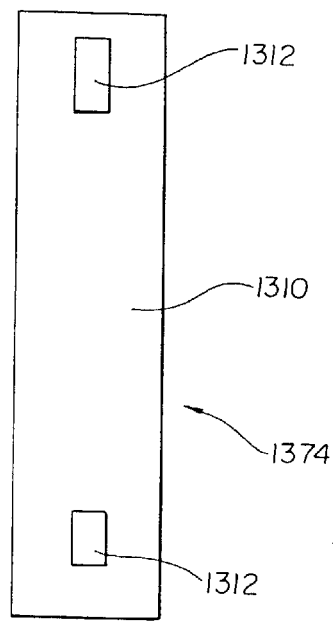
FIG. 33 is a plan view of the keeper of FIG. 31 and FIG. 32.

FIG. 32 and FIG. 33 are plan views of keeper 1374 of FIG. 31. Keeper 1374 includes a body member 1310 and a plurality of tangs 1312. As shown in FIG. 32, tangs 1312 and body member 1310 define a plurality of cavities 1314. In a preferred embodiment, keeper 1374 comprises an injection molded thermoplastic material.

Figure 34:
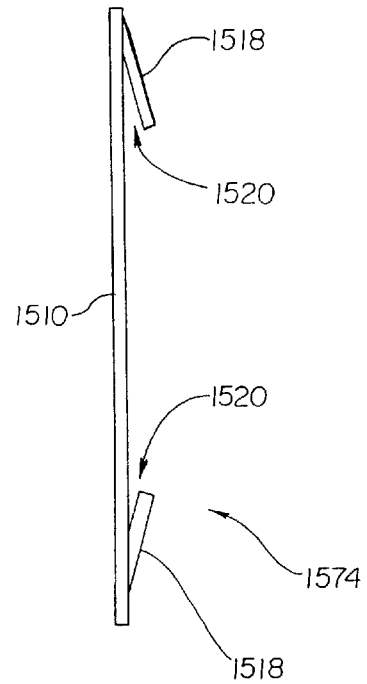
FIG. 34 is a plan view of an additional embodiment of a keeper in accordance with the present invention.
Figure 35:
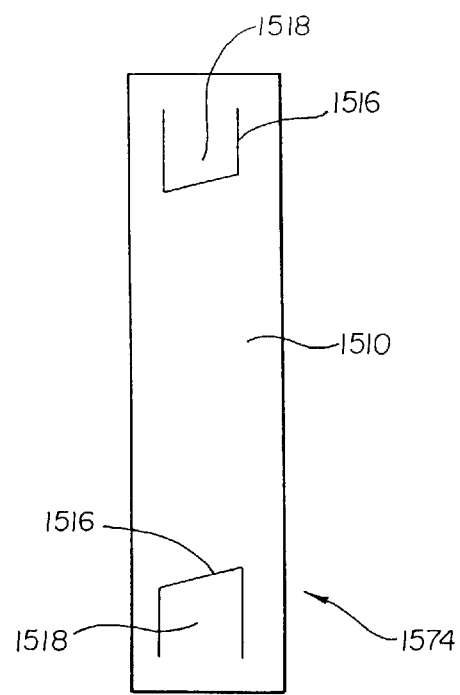
FIG. 35 is a plan view of the keeper of FIG. 34.

FIG. 33 and FIG. 34 are plan views of an additional embodiment of a keeper 1574 in accordance with the present invention. Keeper 1574 includes a body member 1510 and a plurality of slots 1516 defining a plurality of tabs 1518. As best seen in FIG. 34, tabs 1518 and body member 1510 define a plurality of interstitial spaces 1520. In a preferred embodiment, keeper 1574 is adapted to accept a catheter shaft within interstitial spaces 1520 and retain the catheter shaft therein.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter comprising;
   a catheter shaft having a proximal end and a distal end; and
   a rigid keeper fixed to the catheter proximate a proximal end thereof, the rigid keeper having one or more inside surfaces defining a channel adapted to entrap a straight portion of the catheter shaft within a passageway defined by the rigid keeper, wherein the passageway is adapted to allow a curved portion of the catheter to pass into the channel defined by the rigid keeper.

2. The catheter of claim 1, wherein a captured portion of the catheter shaft is disposed within the channel defined by the keeper.

3. The catheter of claim 1, wherein the passageway comprises an opening.

4. The catheter of claim 1, wherein the passageway comprises an arcuate slot.

5. The catheter of claim 1, wherein the channel has a generally cylindrical shape.

6. The catheter of claim 1, wherein the channel has a generally polyhedral shape.

7. The catheter of claim 1, wherein the keeper is fixed to the catheter shaft.

8. The catheter of claim 1, wherein the keeper is fixed to a hub of the catheter.

9. The catheter of claim 1, wherein the keeper is fixed to a strain relief of the catheter.

10. A catheter comprising;
    a catheter shaft having a proximal end and a distal end;
    a keeper fixed to the catheter proximate a proximal end thereof;
    the keeper having a first keeper surface, a second keeper surface and an opening disposed between the first keeper surface and the second keeper surface;
    the keeper having a third keeper surface facing the opening disposed between the first keeper surface and the second keeper surface;
    the keeper having a fourth keeper surface extending between a plane defined by the third keeper surface and a plane extending between the first keeper surface and the second keeper surface;
    a projection extending beyond the third keeper surface in the direction of the opening disposed between the first keeper surface and the second keeper surface; and
    the projection defining a fifth keeper surface.

11. The catheter of claim 10, wherein a captured portion of the catheter shaft is disposed between the third keeper surface and the first keeper surface.

12. The catheter of claim 10, wherein a captured portion of the catheter shaft is disposed between the fourth keeper surface and the fifth keeper surface.

13. The catheter of claim 10, wherein a gap between an end of the projection and a plane extending between the first keeper surface and the second keeper surface is less than a diameter of the shaft.

14. The catheter of claim 10, wherein an end of the projection is generally aligned with a plane extending between the first keeper surface and the second keeper surface.

15. The catheter of claim 10, wherein the projection extends into the opening defined by the first keeper surface and the second keeper surface.

16. The catheter of claim 10, wherein the opening disposed between the first keeper surface and the second keeper surface is adapted to accept a portion of the catheter shaft which has been urged into a curved shape.

17. The catheter of claim 10, wherein the first keeper surface, the second keeper surface, the third keeper surface, the fourth keeper surface, and the fifth keeper surface define a channel.

18. A catheter comprising;
    a catheter shaft having a proximal end and a distal end;
    a keeper fixed to the catheter proximate a proximal end thereof;
    the keeper having a first wall, a second wall, and an opening disposed between the first wall and the second wall;
    the keeper having third wall facing the opening disposed between the first wall and the second wall;
    the keeper having a fourth wall extending between the third wall and the first wall;
    a projection extending beyond the third wall in the direction of the opening disposed between the first wall and the second wall; and
    the projection defining a fifth wall.

19. The catheter of claim 18, wherein a captured portion of the catheter shaft is disposed between the third wall and the first wall.

20. The catheter of claim 18, wherein a captured portion of the catheter shaft is disposed between the fourth wall and the fifth wall.

21. The catheter of claim 18, wherein a gap between an end of the projection and a plane extending between the first wall and the second wall is less than a diameter of the shaft.

22. The catheter of claim 18, wherein an end of the projection is generally aligned with a plane extending between the first wall and the second wall.

23. The catheter of claim 18, wherein the projection extends into the opening defined by the first wall and the second wall.

24. The catheter of claim 18, wherein the opening disposed between the first wall and the second wall is adapted to accept a portion of the catheter shaft which has been urged into a curved shape.

25. The catheter of claim 18, wherein the first wall, the second wall, the third wall, the fourth wall, and the fifth wall define a channel.

* * * * *